(12) United States Patent
Salazar et al.

(10) Patent No.: US 9,907,907 B1
(45) Date of Patent: Mar. 6, 2018

(54) IV HUB LOCK

(71) Applicants: Gilberto A. Salazar, Lucas, TX (US); Jonathan Purcell, Dallas, TX (US)

(72) Inventors: Gilberto A. Salazar, Lucas, TX (US); Jonathan Purcell, Dallas, TX (US)

( * ) Notice: Subject to any disclaimer, the term of this patent is extended or adjusted under 35 U.S.C. 154(b) by 40 days.

(21) Appl. No.: 14/972,672

(22) Filed: Dec. 17, 2015

Related U.S. Application Data

(60) Provisional application No. 62/093,038, filed on Dec. 17, 2014.

(51) Int. Cl.
| | |
|---|---|
| *A61M 25/02* | (2006.01) |
| *A61M 5/168* | (2006.01) |
| *E05B 15/00* | (2006.01) |
| *E05B 35/00* | (2006.01) |
| *E05B 65/00* | (2006.01) |
| *A61M 39/10* | (2006.01) |

(52) U.S. Cl.
CPC .... *A61M 5/16813* (2013.01); *A61M 39/1011* (2013.01); *E05B 15/00* (2013.01); *E05B 35/00* (2013.01); *E05B 65/00* (2013.01)

(58) Field of Classification Search
CPC ........ A61M 2025/024; A61M 39/1011; A61M 25/02; A61M 2025/0246; A61M 2025/0266; A61M 5/1626; A61M 25/0097
USPC ....... 604/158, 174, 175, 177, 178, 180, 905, 604/533–536
See application file for complete search history.

(56) References Cited

U.S. PATENT DOCUMENTS

| | | | | |
|---|---|---|---|---|
| 3,506,007 A | * | 4/1970 | Henkin | A61B 17/3401 604/165.01 |
| 4,392,857 A | * | 7/1983 | Beran | A61M 25/02 128/207.17 |
| 4,795,432 A | | 1/1989 | Karczmer | |
| 4,997,421 A | | 3/1991 | Palsrok et al. | |
| 5,037,405 A | | 8/1991 | Crosby | |
| 5,105,807 A | * | 4/1992 | Kahn | A61M 25/02 128/200.26 |
| 5,697,907 A | * | 12/1997 | Gaba | A61M 5/3205 604/110 |
| 5,910,132 A | | 6/1999 | Schultz | |
| 8,052,649 B2 | * | 11/2011 | Wright | A61M 25/02 604/174 |
| 8,568,372 B2 | | 10/2013 | Woehr et al. | |
| 8,858,505 B1 | | 10/2014 | Justus et al. | |
| 9,339,631 B2 | * | 5/2016 | Graham | A61M 25/0097 |
| 2005/0020977 A1 | | 1/2005 | Eldridge et al. | |

(Continued)

FOREIGN PATENT DOCUMENTS

| | | |
|---|---|---|
| EP | 2077133 | 7/2009 |
| EP | 2168627 | 3/2010 |

*Primary Examiner* — Gerald Landry, II
(74) *Attorney, Agent, or Firm* — Kenneth L Tolar

(57) ABSTRACT

A lock secured around an IV hub includes a hollow barrel having an open upper end with a pair of hinged gates therein that are pivotal between an open and a closed position. Below the gates are a pair of spring-biased flaps that prevent the gates from opening. When a key coupled with a syringe is inserted into slots formed on the gates and rotated, the flaps are forced outwardly, allowing the gates to open with a downward force so that the syringe can be coupled with the IV hub. When the key is rotated in an opposite direction, the flaps automatically pivot toward the center of the barrel and lift the gates to the original closed position.

4 Claims, 2 Drawing Sheets

(56) References Cited

U.S. PATENT DOCUMENTS

| | | | |
|---|---|---|---|
| 2005/0203485 A1* | 9/2005 | Lee | A61M 25/0097 604/523 |
| 2006/0217655 A1* | 9/2006 | Vitullo | A61N 1/36017 604/21 |
| 2008/0294111 A1* | 11/2008 | Tal | A61M 25/0097 604/165.01 |
| 2009/0054843 A1* | 2/2009 | Lundqvist | A61M 5/1415 604/177 |
| 2010/0234811 A1* | 9/2010 | Schubert | A61M 5/326 604/198 |
| 2011/0067623 A1* | 3/2011 | Fagan | G09F 11/23 116/201 |
| 2011/0098654 A1 | 4/2011 | Shipman | |
| 2011/0160655 A1* | 6/2011 | Hanson | A61M 5/1413 604/67 |
| 2012/0227221 A1* | 9/2012 | Whitaker | A61M 39/1011 24/459 |
| 2012/0299290 A1* | 11/2012 | Pisula, Jr. | F16L 37/0982 285/308 |
| 2014/0155866 A1* | 6/2014 | Griffith | A61M 39/10 604/533 |
| 2014/0188087 A1* | 7/2014 | Griesbach, III | A61M 39/1011 604/536 |
| 2014/0228815 A1* | 8/2014 | Haag | A61M 39/10 604/535 |
| 2014/0236088 A1* | 8/2014 | Al-Rashdan | A61M 25/0023 604/164.03 |
| 2014/0257249 A1* | 9/2014 | Witt | A61M 39/1011 604/535 |
| 2014/0364804 A1 | 12/2014 | Stillson | |
| 2016/0089512 A1* | 3/2016 | Siddiqui | A61M 25/0136 604/510 |

* cited by examiner

IV HUB LOCK

CROSS REFERENCE TO RELATED APPLICATIONS

This application is entitled to the benefit of provisional patent application No. 62/093,038 filed on Dec. 17, 2014, the specification of which is incorporated herein by reference.

BACKGROUND OF THE INVENTION

The present invention relates to a lock that prevents injection of unauthorized substances into an IV.

DESCRIPTION OF THE PRIOR ART

An IV is commonly used to inject medications and other fluids into a patient's bloodstream. However, an exposed IV hub allows anyone with a syringe to easily inject unauthorized medications or narcotics, which can dangerously interact with prescribed medications and cause severe side effects or death. Furthermore, if an unauthorized user fails to properly sterilize the IV injection site prior to an infusion, the patient could be exposed to infectious bacteria.

Accordingly, there is currently a need for a device that prevents unauthorized injections into an exposed IV hub. A review of the prior art reveals at least one device that is purportedly designed to prevent unauthorized injections into an IV site. For example, U.S. Pat. No. 8,858,505 issued to Justus et al. discloses a catheter lock comprising a pair of housing sections that are joined to form an enclosure around an injection port. The housing sections include overlying flanges with a fastener attached thereto. The fasteners and flanges interact such that if they are separated, the lock becomes distorted to provide visual evidence of tampering.

Though the device of Justus provides a catheter lock, a locking pin is installed and removed by authorized personnel with a cumbersome hand press that requires manipulation of a lever. Manually operating a hand press is burdensome, strenuous and inconvenient, particularly for those with certain physical ailments. The present invention overcomes the disadvantages of the prior art by providing an IV hub lock that can only be opened by inserting and rotating a uniquely designed key that is coupled with a syringe.

SUMMARY OF THE INVENTION

The present invention relates to a lock including a hollow barrel that is secured around an IV hub. Seated within an open upper end of the barrel are a pair of concave, hinged gates that move between a horizontal, closed position and a substantially vertical, open position. Below the gates are a pair of spring-biased, arcuate flaps that normally prevent the gates from lowering. When a key is inserted into arcuate slots on the gates and rotated, the flaps are forced outwardly toward the barrel periphery, allowing the gates to open with a downward force. When the key is rotated in an opposite direction, the flaps automatically pivot toward the center of the barrel, lift the gates to the closed position and prevent them from reopening when the key is removed.

It is therefore an object of the present invention to provide a lock that prevents unauthorized substances from being injected into an IV site.

It is therefore another object of the present invention to provide a lock for an IV hub that can only be opened with a corresponding key.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
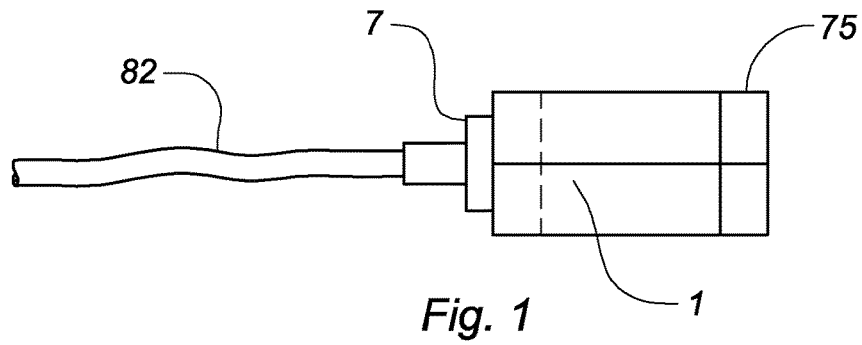
FIG. 1 depicts the lock according to the present invention attached to an IV.
Figure 2:
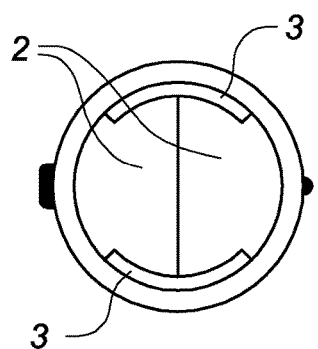
FIG. 2 is a top view of the barrel.
Figure 3:
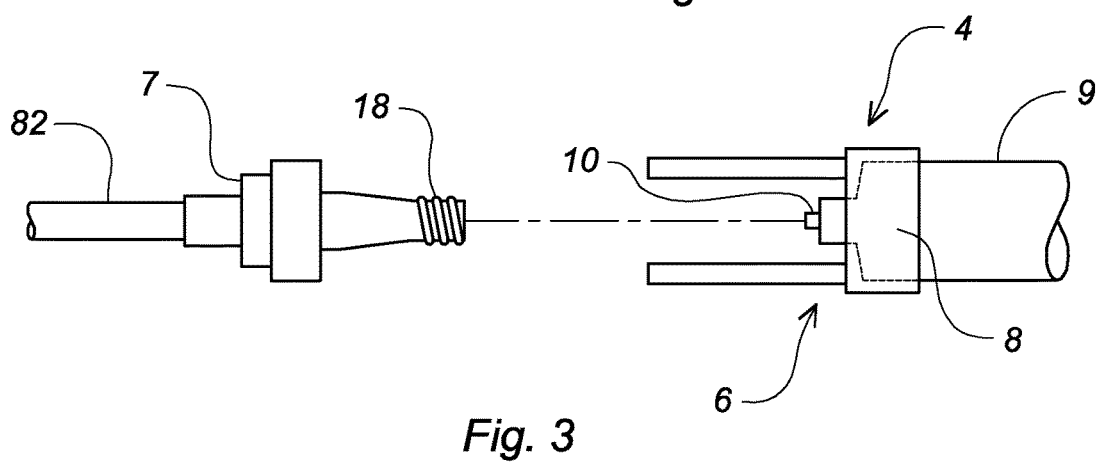
FIG. 3 is an isolated view of the key and IV hub.
Figure 4:
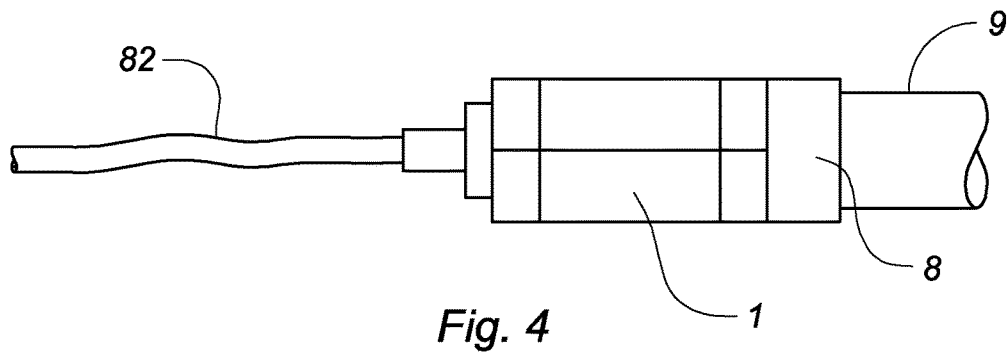
FIG. 4 depicts the lock of FIG. 1 with the key properly engaging the barrel.
Figure 5:
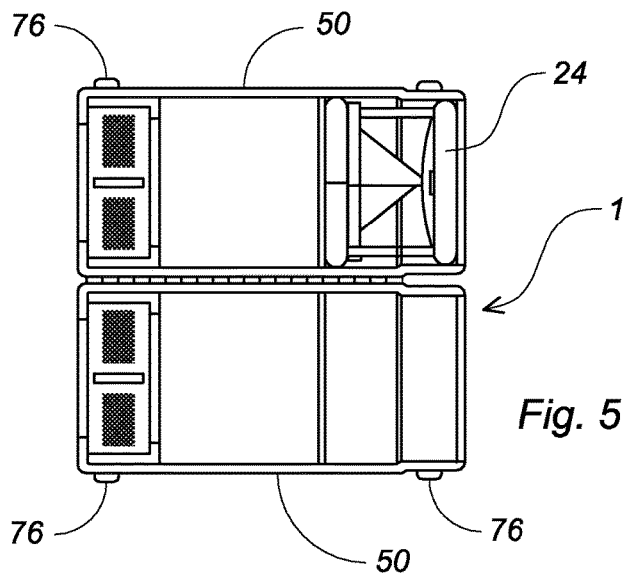
FIG. 5 is an isolated view of the barrel in an open position.
Figure 6:
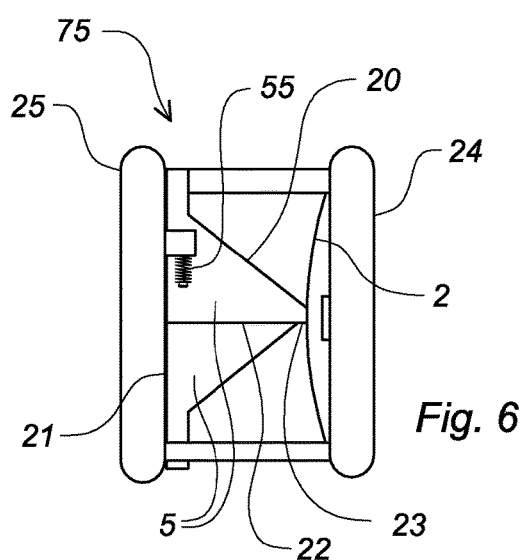
FIG. 6 is an isolated, side view of the locking mechanism, depicting the flaps in a locked position.
Figure 10:
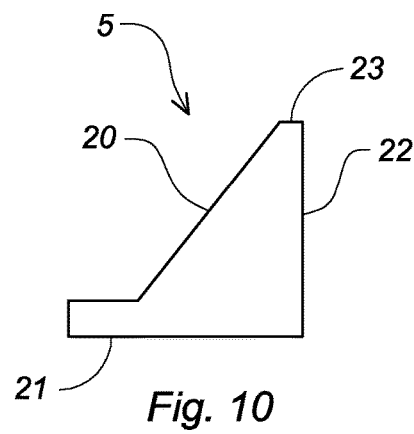
FIG. 10 is an isolated view of an exemplary flap.
Figure 7:
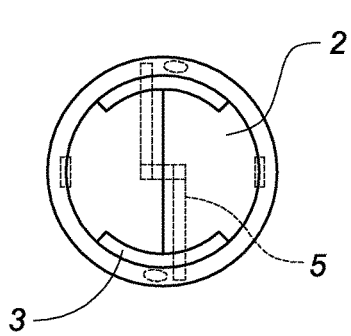
FIG. 7 is top view of the locking mechanism of FIG. 6.
Figure 8:
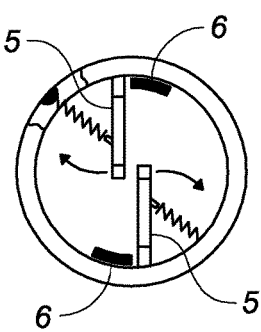
FIG. 8 is a top view of the locking mechanism with the gates omitted to clearly depict the positioning of the key prongs and flaps when in the locked position.
Figure 9:
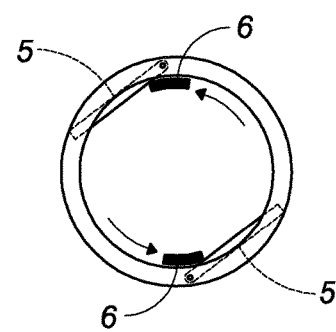
FIG. 9 depicts the locking mechanism of FIG. 8 with the key prongs moving the flaps to the unlocked position.

The present invention relates to an IV hub lock comprising a hollow barrel 1 having an open upper end and an open lower end, both of which are in communication with a hollow interior. Preferably, the barrel is formed of two hinged semi-cylindrical sections 50 that snap together around an IV hub with a non-releasable clamping mechanism 76. Seated within the open upper end is a locking mechanism 75 including an upper ring 24 and a lower ring 25 with a space therebetween. Attached to the upper ring are a pair of concave, hinged gates 2 that move between a substantially horizontal, closed position and a substantially vertical, open position. A pair of opposing, arcuate slots 3 formed around the periphery of the gates receive a key 4 to allow an authorized user to open the gates, as described in more detail, supra.

Below the gates are a pair of arcuate, substantially triangular flaps 5 having a curved, sloped upper edge 20, a lower edge 21, an inner edge 22 and an apex 23 formed at the interface of the inner 22 and upper edges 20. The flaps are pivotally attached to the lower ring and are normally biased by a spring 55 to extend across the center of the barrel, with their inner edges abutting each other. The apex 23 of each triangular flap engages the lower surface of one of the gates to prevent it from opening.

The device further includes a key 4 for opening the gates to allow an authorized medical worker to inject a medication. The key includes a collar 8 having a pair of elongated, arcuate prongs 6 depending therefrom. When the prongs are inserted into the arcuate slots 3 and the collar is rotated, the flaps are forced outwardly toward the barrel periphery, allowing the gates to open with a downward force (from a syringe). When the key is rotated in an opposite direction, the spring-biased flaps automatically pivot toward the center of the barrel while their sloped, curved, upper edges engage and gradually lift the gates to the closed position.

To install the lock according to the present invention, a user seals the barrel around an IV hub 7 attached to an IV tube 82 and having a Luer lock 18 thereon. A syringe 9 having a desired medication is inserted into the key collar 8 and the prongs 6 are inserted into the arcuate slots. The key is rotated in a first direction to pivot the flaps outwardly, allowing the gates to open downwardly. The syringe dispensing nozzle 10 is threadedly coupled with the exposed Luer lock and the medication or fluid is injected. The syringe is then decoupled from the hub and the key is rotated in an opposite direction to allow the flaps to automatically pivot toward the center of the barrel, thereby lifting the gates. The spring-biased flaps remain fixed beneath the gates, preventing them from lowering unless the flaps are again displaced by the designated key. Furthermore, if an unauthorized person attempts to compromise the lock by inserting a pin, needle, wire or other similar tool into one of the slots to move a flap, the other flap apex prevents one of the gates from opening, thereby denying access to the Luer lock.

The above-described device is not limited to the exact details of construction and enumeration of parts provided herein. Furthermore, the size, shape and materials of construction of the various components can be varied without departing from the spirit of the present invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. An IV lock comprising:
    an IV hub having an injection port thereon;
    a barrel enclosing said hub, said barrel having an upper end and a lower end with the upper end proximal said injection port;
    a locking means within the upper end of said barrel for restricting access to said injection port, wherein said locking means includes a pair of hinged gates that are movable between an open position and a closed position, said hinged gates blocking said injection port when in the closed position, a pair of spring-biased flaps engaging said gates to maintain said gates in the closed position, and a means for displacing said spring-biased flaps out of engagement with said gates to allow said gates to open upon application of a force thereto;
    a key for disabling said locking means.

2. The IV lock according to claim 1 wherein said means for displacing said spring-biased flaps out of engagement with said gates comprises:
    said key having a pair of prongs extending therefrom;
    a pair of slots on the upper end of said barrel for receiving said prongs to allow said prongs to engage said flaps whereby rotation of said key in a first direction pivots said flaps outwardly, allowing said gates to open when subjected to the force, and when said key is rotated in an opposite direction, said spring-biased flaps automatically pivot into engagement with said gates.

3. The IV hub lock according to claim 1 further comprising:
    a connector on said injection port;
    said key further having a collar adapted to receive a syringe dispensing nozzle, said dispensing nozzle adapted to couple with said connector on said injection port when said gates are in the open position to permit an authorized injection.

4. The IV lock according to claim 1 wherein said barrel further comprises:
    a pair of semi-cylindrical sections;
    a latch means for securing said semi-cylindrical sections around said IV hub.

\* \* \* \* \*